United States Patent [19]

Vedage et al.

[11] Patent Number: 5,567,847
[45] Date of Patent: Oct. 22, 1996

[54] DISPROPORTIONATION OF AMINES TO PRODUCE SECONDARY AMINES

[75] Inventors: Gamini A. Vedage, Bethlehem; John N. Armor, Orefield, both of Pa.

[73] Assignee: Air Products and Chemicals, Inc., Allentown, Pa.

[21] Appl. No.: 393,145

[22] Filed: Feb. 21, 1995

[51] Int. Cl.$^6$ .................................................. C07C 209/64
[52] U.S. Cl. .................................. 564/493; 564/470
[58] Field of Search .......................... 564/470, 493, 564/395, 415

[56] References Cited

U.S. PATENT DOCUMENTS

| | | | |
|---|---|---|---|
| 2,165,515 | 7/1939 | Schmit | 260/583 |
| 2,540,938 | 2/1951 | Finch et al. | 564/470 |
| 2,781,399 | 2/1957 | Shapiro | 260/583 |
| 3,177,258 | 4/1965 | Rylander et al. | 260/611 |
| 3,673,251 | 6/1972 | Frampton et al. | 260/563 D |
| 4,739,120 | 4/1988 | Zuckerman | 564/385 |
| 5,075,506 | 12/1991 | Zimmerman | 564/490 |
| 5,130,491 | 7/1992 | Zimmerman | 564/490 |
| 5,235,108 | 8/1993 | Borninhof et al. | 564/490 |
| 5,410,086 | 4/1995 | Burgess | 564/470 |

OTHER PUBLICATIONS

Volf, Jiri and Josef Pasek, Prague Institute of Chemical Technology "Hydrogenation of Nitriles" Studies in Surface Science & Catalysis, vol. 27 pp. 105–144 1986.

*Primary Examiner*—Brian M. Burn
*Attorney, Agent, or Firm*—Russell L. Brewer; William F. Marsh

[57] ABSTRACT

This invention relates to an improvement in a process for the production of amines and particularly secondary amines by the hydrogenation of aliphatic and aromatic nitriles and disproportionation of the resulting primary amine containing feedstock. The improvement resides in the use of a bimetallic catalyst comprising nickel or cobalt in combination with rhodium, ruthenium or palladium platinum. Optionally, the catalyst is carried on an alumina support.

11 Claims, No Drawings

5,567,847

DISPROPORTIONATION OF AMINES TO PRODUCE SECONDARY AMINES

FIELD OF THE INVENTION

This invention relates to a disproportionation process for the production of a product slate rich in secondary amines.

BACKGROUND OF THE INVENTION

Catalytic processes for the hydrogenation of aliphatic and aromatic nitriles to produce a product slate rich in primary amines and the subsequent conversion, disproportionation of the primary amines to produce secondary amines are known. The product slate obtained by the hydrogenation of the nitriles may range from primary to secondary to tertiary amines depending upon the particular catalyst and the hydrogenation conditions being used. Typically, nitriles have been hydrogenated to primary or secondary amines using Raney nickel, Raney cobalt, supported nickel and supported cobalt catalysts. Rhodium catalysts have also been used to synthesize secondary amines from nitrile hydrogenation. But, due to the high cost of rhodium these catalysts may not be very practical. Representative patents illustrating the hydrogenation of nitriles to produce various amines and/or disproportionation of an amine containing feedstock are as follows:

U.S. Pat. No. 5,130,491 discloses a method for the production of secondary amines from fatty nitriles, e.g., tallow nitrile, utilizing a nickel catalyst promoted with copper, chromium or molybdenum. Secondary amine production is enhanced by hydrogenating the nitrile in a two-stage process with the second stage being carried out in the absence of ammonia. Temperatures range from 100°–200° C. while pressures range from 50–5000 psig.

U.S. Pat. No. 2,781,399 discloses a process for producing long-chain dialiphatic secondary amines as well as dialkyl and dialkylene amines as well as aromatic secondary amines and aromatic aliphatic secondary amines. The patent notes that the reaction to produce secondary amines is difficult to control and yet obtain a desired secondary amine product of good color and quality at acceptable reaction rates. The catalytic hydrogenation of the aliphatic nitrile is carried out using a nickel catalyst, preferably Raney nickel under anhydrous conditions. Alkali and alkaline earth metal hydroxides addition is undesirable where the feed source contains small amounts of free fatty acids.

U.S. Pat. No. 4,739,120 discloses a process for the hydrogenation of nitriles to primary amine using a rhodium catalyst. The reaction is carried out in the presence of a two phase solvent system comprising an aqueous phase and an immiscible organic phase.

U.S. Pat. No. 5,235,108 discloses a process for preparing secondary alkyl amines by the hydrogenation of alkyl nitriles using a nickel-containing catalyst-containing copper as a promoter. The patent suggests catalytic systems for the hydrogenation of nitriles which include catalyst components of nickel, copper and cobalt as well as dual systems, e.g., nickel-copper chromite and cobalt-copper chromite.

U.S. Pat. No. 3,177,258 discloses a process for the hydrogenation of unsaturated materials, such as unsaturated hydrocarbons and aliphatic and aromatic nitriles. The catalyst used for the hydrogenation is a ruthenium-containing catalyst combined with a platinum metal, e.g., ruthenium combined with platinum, palladium or rhodium. In the hydrogenation of propionitrile, coprecipitated and mixed metal ruthenium-platinum and ruthenium-palladium complexes gave substantial levels of tertiary amine while the ruthenium-rhodium catalyst composition gave high concentrations of secondary amines.

U.S. Pat. No. 3,673,251 discloses a cyclic process for producing mono, secondary and tertiary polyamines by continuously hydrogenating the nitrile in the presence of a hydrogenation catalyst such as cobalt, platinum, palladium, nickel and so forth.

U.S. Pat. No. 5,075,506 discloses a process for producing secondary amines by the hydrogenation of nitriles over a cobalt catalyst promoted with zirconium.

U.S. Pat. No. 2,165,515 discloses a process for the production of amines by the catalytic hydrogenation of nitriles using cobalt and cobalt promoted with barium or manganese.

An article, *Hydrogenation of Nitriles*, J. Volf and J. Posek; Studies in Surface Science & Catalysis, Volume 27, p.105–144, 1986 discloses the hydrogenation of nitriles using a variety of catalysts, e.g., nickel, cobalt, platinum, rhodium, ruthenium and palladium. The effect of these catalysts on product slate is also shown.

SUMMARY OF THE INVENTION

This invention relates to an improved process for the production of amines by the catalytic disproportionation of a feedstock containing primary amines to produce a reaction product rich in secondary amines. In the basic process, a feed stock containing an aliphatic or aromatic primary amine is contacted with hydrogen in the presence of a hydrogenation catalyst, preferably in the absence of ammonia, under conditions conducive for the production of a product slate rich in secondary amines. The improvement in that basic process resides in utilizing catalyst comprising cobalt or nickel in combination with at least one other metal selected from the group consisting of rhodium, palladium, platinum or ruthenium. Preferably, the catalyst is a bimetallic catalyst comprising nickel or cobalt in combination with rhodium, ruthenium or palladium. Optionally, the catalyst is carried on an alumina support.

There are significant advantages associated with the utilization of the catalyst described herein for generating secondary amines. They include:

• an ability to hydrogenate nitriles and generate secondary aliphatic amines in high selectivity;

• an ability to effect disproportionation of primary amines to generate secondary amines within excellent reaction times;

• an ability to reduce catalyst levels required for disproportionation of primary amines for secondary amine formation due to the high activity of the catalyst system; and,

• an ability to operate over an extended period of time without catalyst regeneration.

DETAILED DESCRIPTION OF THE INVENTION

The catalytic process for the hydrogenation of aliphatic and aromatic nitriles to produce a feedstock containing primary amines using the catalysts described herein is carried out using procedures commonly used in the art. Catalytic hydrogenations can be performed on a variety of aliphatic nitriles including aliphatic mononitriles and aliphatic dinitriles. Exemplary nitriles include $C_{2-10}$ aliphatic nitriles such as acetonitrile, propionitrile, butyronitrile, valeronitrile, capronitrile, 2,2-dimethylpropanenitrile, glutaronitrile, adiponitrile, biscyanoethylether, malononitrile and 1,3,5-tricyanopentane. Cycloaliphatic nitriles include cyclobutanecarbonitrile, cyclopentanecarbonitrile and so forth. The process is also adapted for the hydrogenation of aromatic nitriles, and representative aromatic nitriles include benzonitrile, phenylacetonitrile, p-tolunitrile, aminobenzonitrile, naphthylnitrile and so forth.

Disproportionation of primary amines to secondary amines as shown by the equation

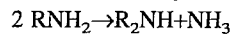

not only can be effected with primary amines generated by the above nitrile hydrogenation process, disproportionation of other amines, e.g., alkylene amines and polyalkylene polyamines can also be effected. Examples include ethylamine, ethylenediamine, diethylenetriamine, triethylene, tetramine and so forth.

The catalyst used in effecting hydrogenation of the nitriles and the disproportionation of the reaction product containing primary amines is one containing cobalt or nickel in combination with the noble metals: rhodium, ruthenium, palladium or platinum. The metals are preferably carried on a support conventionally used for these types of processes, such supports being alumina, carbon, kieselguhr, bentonite, titania, silica, silica-alumina, zirconium oxide, and the like. The supports are generally inert but they may be active so long as they do not adversely interfere with the hydrogenation or disproportionation processes. For reasons of efficiency and economy the preferred support is alumina.

The cobalt or nickel metal component of the catalyst, including the support for disproportionation generally is present in an amount from about 1 to 60% by weight and preferably about 5 to 25% by weight. The other metallic component e.g. rhodium, ruthenium, platinum or palladium, is present in an amount from 0.01 to about 10% by weight, preferably from about 0.5 to 2% by weight. The metal components of the catalyst preferably are present as a bimetallic catalyst, i.e., at least two of the metals are present on the same support. This is in contrast to a catalyst in the form of a physical mixture. That situation exists where the cobalt or nickel, or possibly both, are each carried on an alumina support and the other metallic component(s) carried on a separate alumina support. The resulting catalyst then is formed by blending the catalyst components together in appropriate ratios.

The catalyst levels used in effecting disproportionation of the amines are those commonly used in conventional hydrogenation/disproportionation processes of this type. Broadly, the catalyst loading, as a percent of the aliphatic or aromatic amine containing feedstock is from about 0.1 to about 10% by weight. Conventional levels are more commonly within a range from about I to 5% by weight. The level of catalyst employed is one that can be appropriately selected by the practitioner.

Conditions effective for disproportionating the aliphatic and aromatic primary amine feedstock are those conventionally used in the prior art, although the process is highly effective at relatively low pressures, e.g., from about atmospheric to about 1000 psig. Temperatures for hydrogenation typically range from about 60° to 200° C. with the hydrogenation reaction preferably being carried out at the temperature of 170° to 190° C. As with conventional disproportionation reaction, a solvent may be used in the process although one is not necessary. Conventional solvents include those organic solvents such as the aromatic hydrocarbons, e.g., benzene, toluene, xylene, chlorinated hydrocarbons such as chlorobenzene, dichlorobenzene, bromobenzene, dibromobenzene, and aliphatic solvents such as cyclohexane, cycloheptane, tetrahydrofuran, dioxane, and so forth may be used.

The utilization of multi-metal component catalysts, particularly bimetallic catalysts wherein the metals are carried on the same support, e.g., as in the coprecipitation of multi-metal salt solutions onto the support, not only enhances the rate of hydrogenation of the nitrile to the primary amine, but also enhances the rate of disproportionation of the primary amine to secondary amines. The presence of the multi-metal components in the catalyst system acts synergistically in the sense that better results are obtained with the catalyst combination than when each catalytic component is used individually. Surprisingly, too, the proportion of secondary amine produced in the hydrogenation and in the disproportionation of the primary amine feedstock is not directly related to the proportion of the individual metals, particularly the secondary metals, e.g., rhodium, ruthenium, platinum or palladium, in the catalyst system. One might expect an "averaging" effect when incorporating such metals with cobalt or nickel. As is known cobalt and nickel tend to produce primary amines in preference to the secondary and tertiary amines, while palladium tends to produce secondary and tertiary amines. Yet, a small amount of platinum or the palladium component results in secondary amine concentrations that is not proportional to the concentration of palladium in the catalyst system.

The disproportionation of the primary amine, or alternatively, the formation of the secondary amine, can be enhanced by altering the disproportionation conditions. As one might expect from the prior art, disproportionation of the primary amine to secondary amine is enhanced through the removal of ammonia from the reaction medium. This can be accomplished through a reduction in pressure. Elevation of reaction temperature can also be effective in aiding disproportionation of the amine containing feedstock. The temperature for enhanced disproportionation ranges from about 140° to 220° C. and preferably from about 180° to 200° C. Pressures for disproportionation may range from 50 to 500 psig.

The following examples are provided to illustrate various embodiments of the invention and are not intended to restrict the scope thereof.

EXAMPLE 1

Production of Butylamines

Disproportionation at 180° C., 500 psig

Using Nickel Catalysts

Butyronitrile was hydrogenated to a product slate containing amines and then disproportionated to form a product rich in secondary amines by the following procedure. The selective secondary amine synthesis was done in a batch reactor in two steps. First, the nitrile was hydrogenated at 125° C. and 500 psig pressure to completion. Then, the primary amine containing reaction product was disproportionated . To accomplish this, the reactor was vented to remove ammonia and fresh hydrogen added. Disproportionation was done at 180° C. or 195° C. at either 500 or 100 psig to produce secondary amines in high selectivity. The procedures set forth in more detail are as follows.

Catalyst Preparation

Several catalysts were prepared by precipitation of salt solutions onto an alumina support. Bimetallic catalysts containing more than one metal were obtained by coprecipitating solutions of metal salts onto a single alumina support. After the catalyst was prepared, the catalyst was reduced at 500° C. in the presence of hydrogen. Hydrogenation or reduction of the catalyst was accomplished by charging the catalyst to a ½" ID tubular reactor wherein hydrogen was passed over the catalyst at a rate of 20–30 cc/min. After 10 min. of purging the reactor, the contents were heated to 500° C. The system was held at temperature for 1 hr, cooled to room temperature, and purged with nitrogen for 30 min. The reduced catalyst was then recovered in air at room temperature.

Hydrogenation Procedure to Produce Primary Amine Containing Feedstock

A 300 cc autoclave reactor was used with all hydrogenations carried out at 1500 rpm stirring rate to minimize hydrogen mass transfer as a limitation to reaction rates. The desired pre-reduced catalyst charge was weighed and added to the pressure vessel. The feed was then added to the reactor. The reactor was closed, leak tested and purged three times with nitrogen and then purged three times with hydrogen. The reactor was then pressurized with hydrogen to 500 psig and heated to the desired reaction temperature with agitation. When tile reaction temperature was reached, the reactor pressure was adjusted to 500 psig. The reactor was connected through a pressure controller to a ballast tank filled with hydrogen. The volume and hydrogen pressure of the ballast tank was chosen to be sufficient to provide all of the hydrogen necessary for the reaction without dropping below 500 psig. The volume was also small enough so that the ballast pressure drop during the reaction gave an accurate measure of the hydrogen consumed. The ballast pressure was followed versus time as a measure of the hydrogenation taking place. By calculating, the ballast pressure change (known volume), the molar hydrogen consumption was determined. When the reaction test was completed, the ballast line was closed, the reactor cooled and purged with nitrogen. The reaction mixture was then removed through the charge line/filter. Catalyst life studies were done by adding the feed through the charge line/filter and repeating the procedure except for the activation of the catalyst.

Disproportionation Procedure

After the nitrile was hydrogenated at 125° C. and 500 psi pressure to completion, selective secondary amine synthesis was accomplished as follows. First, the reactor was vented to remove ammonia and fresh hydrogen added. Then, the reactor contents were heated to either 180° C. or 195° C. for 135 minutes at either 100 or 500 psig to produce secondary amines in high selectivity. Table 1 provides the conditions and results of hydrogenation and disproportionation (180° C./500 psi pressure) of butyronitrile to secondary amines.

TABLE 1

Hydrogenation of 100 g butyronitrile at 125° C. and 500 psi pressure and disproportionation of the product at 500 psi and 180° C. at a catalyst loading of 1.5 wt % of nitrile

| CATALYST | Action | Time (min.) | Press. (psi) | Temp. (°C.) | $BuNH_2^a$ (%) | $Bu_2NH^b$ (%) | $Bu_3N^c$ (%) |
|---|---|---|---|---|---|---|---|
| Raney Ni | H | 116 | 500 | 125 | 77.9 | 21.3 | 0.2 |
|  | D | 135 | 500 | 180 | 61.6 | 38.1 | 0.3 |
| 20% Ni/Al$_2$O$_3$ | H | 260 | 500 | 125 | 65.4 | 33.7 | 0.9 |
|  | D | 135 | 500 | 180 | 55.3 | 43.4 | 1.3 |
| 20% Ni/1% Ru/Al$_2$O$_3^d$ | H | 104 | 500 | 125 | 67.7 | 31.1 | 1.2 |
|  | D | 135 | 500 | 180 | 46.5 | 51.9 | 1.6 |
| 20% Ni/1% Cu/Al$_2$O$_3$ | H | 320 | 500 | 125 | 63.0 | 34.9 | 2.1 |
|  | D | 135 | 500 | 180 | 54.3 | 43.3 | 2.4 |
| 20% Ni/1% Pd/Al$_2$O$_3^d$ | H | 66 | 500 | 125 | 64.5 | 34.5 | 1.0 |
|  | D | 135 | 500 | 180 | 30.9 | 67.5 | 1.6 |
| 20% Ni/1% Rh/Al$_2$O$_3^d$ | H | 74 | 500 | 125 | 70.4 | 29.2 | 0.4 |
|  | D | 135 | 500 | 180 | 45.4 | 53.6 | 0.9 |
| Feed |  |  |  |  | 72.0 | 28.0 | 0.0 |
| 1% Pd/Al$_2$O$_3$ | D | 135 | 500 | 180 | 71.3 | 28.7 | 0.0 |
| Feed |  |  |  |  | 73.9 | 26.1 | 0.0 |
| 20% Ni/Al$_2$O$_3$ + 1% Pd/Al$_2$O$_3^e$ | D | 135 | 500 | 180 | 63.5 | 36.5 | 0.0 |

$^a$BuNH$_2$ = butylamine;
$^b$Bu$_2$NH = dibutylamine;
$^c$Bu$_3$N = tributylamine;
$^d$refers to a bimetallic catalyst;
$^e$refers to a physical mixture of the catalyst metals;
H  refers to the step of hydrogenation of the nitrile;
D  refers to the step of disproportionation;
Press. refers to the gauge pressure employed for the hydrogenation of the nitrile in Step H and to the pressure for the disproportionation of the hydrogenated reaction product in Step D;
Temp. refers to the temperature used for hydrogenation (H) and for disproportionation (D);
Time at temperature refers to the reaction time for the hydrogenation (H) and for disproportionation (D).

The results in Table 1 show the results of the disproportionation of a mixture of primary and secondary amines with nickel and nickel bimetallic catalysts. The nickel catalyst resulted in an increase of secondary amines from 33.7 to 43.4% while the nickel palladium bimetallic catalyst increased from 34.5 to 67.5 %. For the palladium catalyst alone, the secondary amine increased from 28 to 28.7%. The physical mixture of a nickel and a palladium catalyst increased secondary amine formation from 26.1 to 36.5%.

There is as small increase with a physical mixture, but that increase on a percentage basis is not equivalent to the unexpectedly large increases obtained with the bimetallic catalysts. As shown in Table 1, the selectivity to secondary amines by the hydrogenation of butyronitrile and the subsequent disproportionation of the butylamine decreases in the order:

20%Ni/1%Pd/$Al_2O_3$>20%Ni/1%Rh/$Al_2O_3$>20%Ni/1%Ru/$Al_2O_3$

>20%Ni/$Al_2O_3$>20%Ni/$Al_2O_3$1%+Pd/$Al_2O_3$>20%Ni/1%Cu/$Al_2O_3$>Raney Ni

>Pd/$Al_2O_3$

The highest selectivity to secondary amines is seen with 20%Ni/1%Pd/$Al_2O_3$ bimetallic catalyst (67.5% secondary amines) and the lowest was seen with the prior art catalysts, Raney Nickel, 20%Ni/1%Cu/$Al_2O_3$, and 20%Ni/$Al_2O_3$ catalysts (~40%).

EXAMPLE 2

Disproportionation at 180° C. 100 psig Using Nickel Catalysts

The procedure of Example 1 was repeated except that disproportionation was carried out at 100 psig as opposed to 500 psig in order to determine the effect of pressure. Table 2 sets forth the conditions and results.

1%Pd/$Al_2O_3$ catalyst, the level of secondary amines increased to 79.5% (from 67.5) when the hydrogen pressure during disproportionation was decreased from 500 psig to 100 psig. With the 20%Ni/1%Ru/$Al_2O_3$ catalyst, lowering the pressure to 100 psi increased the level of secondary amines to 72.1% from 51.9%. Under the same conditions the 20%Ni/1%Cu/$Al_2O_3$ gave only 53.3% secondary amines. These results clearly show that the rate of disproportionation to secondary amines increases at lower hydrogen pressures. These results also show that the nickel bimetallic catalysts were superior to the prior art Ni/Cu catalyst.

EXAMPLE 3

Disproportionation at 195° C., 500 psig. Using Nickel Catalysts

The procedure of Example 1 was repeated except that disproportionation was carried out at 195° C. instead of 180° C. Table 3 sets forth the conditions and results.

TABLE 2

Hydrogenation Of 100 g Butyronitrile At 125° C. And 500 psi Pressure And Disproportionation Of The Product At 100 psi And 180° C. At A Catalyst Loading Of 1.5 wt % Of Nitrile

| CATALYST | Action | Time (min.) | Press. (psi) | Temp (°C.) | $BuNH_2$[a] (%) | $Bu_2NH$[b] (%) | $Bu_3N$[c] (%) |
|---|---|---|---|---|---|---|---|
| 20% Ni/1% Pd/$Al_2O_3$[d] | H | 70 | 500 | 125 | 64.4 | 34.5 | 1.0 |
|  | D | 135 | 100 | 180 | 14.7 | 79.5 | 5.7 |
| 20% Ni/1% Ru/$Al_2O_3$[d] | H | 100 | 500 | 125 | 74.3 | 25.3 | 0.4 |
|  | D | 135 | 100 | 180 | 24.7 | 72.1 | 3.2 |
| 20% Ni/1% Cu/$Al_2O_3$[d] | H | 200 | 500 | 125 | 57.3 | 36.1 | 5.5 |
|  | D | 135 | 100 | 180 | 40.7 | 53.3 | 6.0 |

[a,b,c,d],H and D Same as Table 1

Table 2 shows the results for the hydrogenation of butyronitrile at 125° C. and 500 psi and disproportionation of the product at 180° C. and 100 psi pressure. As shown in Table

TABLE 3

Hydrogenation Of 100 g Butyronitrile At 125° C. And 500 psi Pressure And Disproportionation Of The Product At 500 psi And 195° C. At A Catalyst Loading Of 1.5 wt % Of Nitrile

| CATALYST | Action | Time (min.) | Press. (psi) | Temp. (°C.) | $BuNH_2$[a] (%) | $Bu_2NH$[b] (%) | $Bu_3N$[c] (%) |
|---|---|---|---|---|---|---|---|
| 20% Ni/1% Pd/$Al_2O_3$[d] | H | 80 | 500 | 125 | 64.4 | 34.5 | 1.0 |
|  | D | 240 | 500 | 195 | 10.6 | 83.6 | 5.7 |
| 20% Ni/1% Pd/$Al_2O_3$[d] | H | 100 | 500 | 125 | 67.6 | 31.9 | 0.6 |
|  | D | 180 | 500 | 195 | 14.6 | 81.3 | 4.1 |
| 20% Ni/1% Rh/$Al_2O_3$[d] | H | 60 | 500 | 125 | 70.4 | 29.2 | 0.4 |
|  | D | 240 | 500 | 195 | 13.9 | 81.1 | 4.9 |

[a,b,c,d],H and D Same as Table 1

2, vis-a-vis Table 1, the rate of disproportionation of a primary amine containing feedstock to secondary amines increases at lower hydrogen pressure. With the 20%Ni/

Table 3 shows the effect of temperature on disproportionation activity. As shown in Table 3, vis-a-vis Table 1, by increasing the temperature during disproportionation one increases the rate of disproportionation or primary amines to secondary amines. With the 20%Ni/1%Pd/Al$_2$O$_3$ catalyst, increasing the disproportionation temperature from 180° C. to 195° C. increased secondary amine formation from 67% to 84% (Compare Tables 1 & 3 ). Extending the disproportionation time from 180 to 240 minutes enhanced secondary amine formation only slightly. This shows the catalyst was fairly active and reaction was complete within the 180 minute time frame. With the 20%Ni/1%Rh/Al$_2$O$_3$ catalyst, the secondary amine formation increased from 53% to 81%.

EXAMPLE 4

Disproportionation Butyronitrile At 180° C. And 500 Psi Using Cobalt Catalysts

The procedure of Example 1 was repeated except that cobalt was substituted for the nickel component in generating the catalysts. Table 4 sets forth the conditions and results.

gave 67% secondary amines while Co/Pd only gave 45% selectivity to secondary amines.

EXAMPLE 5

Disproportionation Of Butyronitrile At 180° C., 100 psi

Using Cobalt Catalysts

The procedure of Example 4 was repeated except that the disproportionation of the feedstock was done at 100 psig rather the 500 psig. Table 5 sets forth the results.

TABLE 4

Hydrogenation Of 100 g Butyronitrile And Disproportionation Of The Product At 180° C. And 500 Psi Pressure At A Catalyst Loading Of 1.5 wt % Of Nitrile

| CATALYST | Action | Time (min.) | Press. (psi) | Temp. (°C.) | BuNH$_2$[a] (%) | Bu$_2$NH[b] (%) | Bu$_3$N[c] (%) |
|---|---|---|---|---|---|---|---|
| 20% Co/1% Pd/Al$_2$O$_3$[d] | H | 500 | 500 | 125 | 65.1 | 33.4 | 0.5 |
|  | D | 135 | 500 | 180 | 63.9 | 34.3 | 1.9 |
| 20% Co/1% Rh/Al$_2$O$_3$[d] | H | 300 | 500 | 125 | 54.8 | 42.9 | 0.5 |
|  | D | 135 | 500 | 180 | 48.5 | 50.8 | 0.7 |
| 20% Co/10% Ni/Al$_2$O$_3$[d] | H | 200 | 150 | 500 | 78.2 | 21.4 | 0.4 |
|  | D | 135 | 500 | 180 | 71.1 | 28.4 | 0.4 |

[a,b,c,d]H and D Same as Table 1

As shown in Table 4, the selectivity to secondary by hydrogenation/disproportionation of butyronitrile decreases in the order:

20%Co/1%Rh/Al$_2$O$_3$ >20%Co/1%Pd/Al$_2$O$_3$

TABLE 5

Hydrogenation Of 100 g Butyronitrile And Disproportionation Of The Product At 180° C. And 100 Psi Pressure At A Catalyst Loading Of 1.5 wt % Of Nitrile

| CATALYST | Action | Time (min.) | Press. (psi) | Temp (°C.) | BuNH$_2$[a] (%) | Bu$_2$NH[b] (%) | Bu$_3$N[c] (%) |
|---|---|---|---|---|---|---|---|
| 20% Co/1% Pd/Al$_2$O$_3$[d] | H | 110 | 500 | 150 | 53.0 | 44.8 | 2.2 |
|  | D | 135 | 100 | 180 | 29.6 | 66.2 | 4.2 |
| 20% Co/1% Rh/Al$_2$O$_3$[d] | H | 190 | 500 | 125 | 61.5 | 38.2 | 0.3 |
|  | D | 135 | 100 | 180 | 40.1 | 58.7 | 1.3 |

[a,b,c,d]H and D Same as Table 1

The 20%Co/1%Rh/Al$_2$O$_3$ and 20%Co/1%Pd/Al$_2$O$_3$ bimetallic catalysts showed higher disproportionation activity than the bimetallic cobalt/nickel catalyst while 10%Co/10%Ni/Al$_2$O$_3$ catalyst showed excellent hydrogenation activity but lower disproportionation activity. Further, if one compares results obtained with Ni/M (M=Rh, Ru and Pd) bimetallic catalysts to the Co/M catalysts and to the individual catalyst components for secondary amine synthesis, one observes that the Ni/M bimetallic catalysts have higher disproportionation activity than Co/M (M=Rh, Ru of Pd) bimetallic catalysts. For example, for hydrogenation of butyronitrile and disproportionation of the amine reaction product at 180° C. and 500 psi pressure, the Ni/Pd catalyst Table 5 gives the results for hydrogenation/disproportionation of butyronitrile at 180° C. and 100 psi pressure. Inspection of Tables 4 & 5 provides a comparison of disproportionation activity at both 500 psi and 100 psi pressure. It is clear from these tables that a lower hydrogen partial pressure in the disproportionation of an amine containing feed stock increases the rate of disproportionation.

The results of Table 5 shows that hydrogenation/disproportionation of butyronitrile at 180° C. and 100psi pressure decreases in the order:

20%Co/1%Pd/Al$_2$O$_3$>20%Co/1%Rh/Al$_2$O$_3$>>20%Co/Al$_2$O$_3$

Once again the Ni/M (M=Rh, Ru or Pd) bimetallic catalysts show higher levels of secondary amines than Co/M bimetallic catalysts for disproportionation at 180° C. and 100 psi pressure. For example, at 100 psi conditions the Ni/Pd catalyst resulted in 80% secondary amine formation while the Co/Pd catalyst resulted in 66% secondary amine formation. However, both sets of catalysts were highly active and resulted in excellent selectivity to secondary amine formation.

EXAMPLE 6

Disproportionation of Butyronitrile at 195° C. 100 psi Using Cobalt Catalysts The procedure of Example 5 was repeated except that the disproportionation was extended from 135 min. to 240 min and the temperature increased to 195° C. Table 6 shows the effect of extended reaction time and increased temperature on activity and selectivity.

TABLE 6

Hydrogenation Of Butyronitrile And Disproportionation Of The Hydrogenated Product At 195 C. And 100 Psi Pressure At A Catalyst Loading Of 1.5 wt % Of Nitrile

| CATALYST | Action | Time (min.) | Press. (psi) | Temp (°C.) | $BuNH_2^a$ (%) | $Bu_2NH^b$ (%) | $Bu_3N^c$ (%) |
|---|---|---|---|---|---|---|---|
| 20% Co/1% Ru/Al$_2$O$_3$ | H | 290 | 500 | 150 | 78.1 | 21.9 | 0.0 |
| | D | 240 | 100 | 195 | 34.5 | 64.0 | 1.5 |
| 20% Co/1% Rh/Al$_2$O$_3$ | H | 150 | 500 | 125 | 59.8 | 39.6 | 0.5 |
| | D | 240 | 100 | 195 | 24.4 | 73.0 | 2.6 |
| 20% Co/1% Pd/Al$_2$O$_3$ | H | 100 | 500 | 150 | 54.8 | 42.8 | 2.3 |
| | D | 240 | 100 | 195 | 7.3 | 81.2 | 11.1 |
| 20% Co/Al$_2$O$_3$ | H | 300 | 500 | 180 | 65.1 | 34.4 | 0.5 |
| | D | 240 | 100 | 195 | 36.3 | 59.5 | 1.8 | a,b,c,d,H and D   Same as Table 1

By inspection of Table 5 & 6, it is clear that by increasing the temperature and increasing the time of disproportionation one can increase the rate of disproportionation to secondary amines. With 20%Co/1%Pd/Al2O3 catalyst, increasing the disproportionation temperature from 180° C. to 195° C. at 100 psi pressure increased the secondary amines from 66% to 81%. With 20%Co/1%Rh/Al2O3 catalyst, the same increase in temperature increased the secondary amines from 59% to 72%. The 20%Co/Al2O3 was the least effective in disproportionating the primary amine containing feedstock.

EXAMPLE 7

Two Stage Disproportionation At 180° C., 50 psi Using Cobalt

The procedure of Example 4 was repeated in that disproportionation was carried out at 195° C. using cobalt catalysts. A two stage disproportionation was utilized in an effort to optimize the level of secondary amine formation. First, hydrogenation of the butyronitrile was effected and the resulting product, after venting to remove ammonia, subjected to disproportionated for 135 min. After the first disproportionation the reactor was sampled and vented again to remove ammonia and a second disproportionation was carried out for another 135 min. The conditions and results are shown in Table 7.

TABLE 7

Hydrogenation Of 100 g Butyronitrile And Disproportionation Of The Product At 180° C. And 50 and 100 Psi Pressure At A Catalyst Loading Of 1.5 wt % Of Nitrile

| CATALYST | Action | Time (min.) | Press. (psi) | Temp (°C.) | $BuNH_2^a$ (%) | $Bu_2NH^b$ (%) | $Bu_3N^c$ (%) |
|---|---|---|---|---|---|---|---|
| 20% Co/1% Rh/Al$_2$O$_3^d$ | H | 150 | 500 | 125 | 57.6 | 41.6 | 0.8 |
| 1st | D | 135 | 50 | 195 | 26.3 | 71.9 | 1.8 |
| 2nd | D | 135 | 50 | 180 | 8.2 | 88.7 | 2.9 |
| 20% Co/1% Pd/Al$_2$O$_3^d$ | H | 110 | 500 | 150 | 53.0 | 44.8 | 2.2 |
| 1st | D | 135 | 100 | 180 | 29.6 | 66.2 | 4.2 |
| 2nd | D | 135 | 100 | 180 | 8.0 | 83.7 | 8.1 | a,b,c,d,H and D   Same as Table 1

It is clear from Table 7, as in Tables 1 and 2, that lower hydrogen partial pressure increases secondary amine formation and the rate of disproportionation. As shown in Table 7, with the 20%Co/1%Rh/Al2O3 catalyst a reaction product with 89% secondary amine was produced while the 20%Co/

1%Pd/Al2O₃ produced a reaction product with 84% secondary amines. Our results show that by varying disproportionation temperature and hydrogen and ammonia partial pressures, the secondary amine selectivity can be increased to >85%.

EXAMPLE 8

Disproportionation of Butylamine in Plug Flow Reactor

The general procedure for effecting disproportionation as described in Example 1 was repeated except that the feedstock consisted of butylamine and the reaction was carried out in a continuous plug flow reactor instead of a batch reactor. The plug flow reactor was ½ inch in diameter and 1 foot long. It was filled with 6 cc (5 g) of catalyst. The gas hourly space velocity (GHSV) of the butylamine feed was 1100. The feed rates were 17 cc/hr of amine, 1 L/hr of hydrogen. Table 8 sets forth the conditions and results for the testing of nickel and cobalt based catalysts.

Al₂O₃ and 20%Co/1%Pd/Al₂O₃ catalyst had similar activity (~ 43%). As the temperature was raised the 20%Co/1%Pd/Al₂O₃ catalyst had higher activity with 77% conversion at 180° C. while a selectivity of 61% at 184° C. for 20%Co/Al₂O₃ catalyst was obtained. With these cobalt catalysts the selectivity to secondary amines are high until the conversion reaches about 80% and falls drastically at higher conversions. A cobalt catalyst when used alone produces secondary amine but conversion is relatively low.

The results show two important features. The first advantage is that the bimetallic Co and Ni catalysts have higher disproportionation activity than 20% Ni/Al₂O₃ and 20% Co/Al₂O₃ catalysts. The second advantage of using these bimetallic catalysts is that they have higher selectivity for the disproportionation of primary amines to secondary amines than either 20% Ni/Al₂O₃ or 20% Co/Al₂O₃.

These results suggest that the second metal in the bimetallic catalyst increases disproportionation activity and it also plays a role in determining selectivity at high conversion. Also, the Ni-Pd bimetallic catalyst, gives higher ter-

TABLE 8

Disproportionation of Butylamine in Plug flow Reactor with 5 g Catalyst

| Catalyst[a] | Temp. (°C.) | Butylamine flow rate cc/hr | H₂ flow rate cc/hr | Press. (PSI) | Conversion of Butylamine (%) | Selectivity to Products (%) | |
|---|---|---|---|---|---|---|---|
| | | | | | | dibutylamine | tributylamine |
| 20% Ni/Al₂O₃ | 165° C. | 17 | 1000 | 189 | 79 | 96.5 | 3.5 |
| | 184° C. | 17 | 1000 | 180 | 93 | 71.7 | 28.3 |
| 20% Ni/1% Pd/Al₂O₃ | 165° C. | 17 | 1000 | 178 | 89 | 78.1 | 21.8 |
| | 188° C. | 17 | 1000 | 177 | 95 | 53.2 | 46.8 |
| 20% Ni/1% Ru/Al₂O₃ | 164° C. | 17 | 1000 | 175 | 94 | 87.1 | 12.9 |
| | 187° C. | 17 | 1000 | 173 | 95 | 53.6 | 46.5 |
| | 155° C. | 17 | 1000 | 179 | 90 | 95.9 | 4.1 |
| 20% Co/Al₂O₃ | 166° C. | 17 | 1000 | 156 | 45 | 96.7 | 3.3 |
| | 184° C. | 17 | 1000 | 153 | 61 | 97.0 | 3.0 |
| | 200° C. | 17 | 1000 | 172 | 78 | 89.0 | 11.0 |
| 20% Co/1% Pd/Al₂O₃ | 165° C. | 17 | 1000 | 156 | 42 | 96.1 | 3.9 |
| | 180° C. | 17 | 1000 | 136 | 77 | 89.3 | 10.8 |
| | 190° C. | 17 | 1000 | 155 | 90 | 79.5 | 20.5 |

As shown in Table 8 the activity of these catalysts for the conversion of butylamine to secondary and tertiary butylamines decrease in the order: (at ~90% conversion)

20%Ni/1%Pd/Al₂O₃=20%Ni/1%Ru/Al₂O₃
>20% Ni/Al₂O₃>20%Co/1%Pd/Al₂O₃>20%Co/Al₂O₃

The nickel based catalysts clearly have higher activity than cobalt based catalysts. At 165° C., 20%Ni/1%Pd/Al2O₃ and 20%Ni/1%Ru/Al₂O₃ catalysts have higher activity than 20%Ni/Al₂O₃ catalyst, but as the temperature is raised the activity of these catalysts appear to merge together. The 20%Ni/1%Ru/Al₂O₃ catalyst had similar activity to 20%Ni/1%Pd/Al₂O₃ catalyst but the selectivity to secondary amines was much better with Ni-Ru catalyst than NioPd catalyst. The 20%Ni/1%Pd/Al₂O₃ catalyst at 165° C. gave 90% conversion with 78% selectivity to dibutylamine. On the other hand, the 20%Ni/1%Ru/Al₂O₃ catalyst at 165° C. gave 93% conversion and 87% selectivity to dibutylamine. When the reactor temperature was lowered to 155° C. the 20%Ni/1%Ru/Al₂O₃ catalyst gave 90% conversion with 96% selectivity to dibutylamine. With 20%Ni/Al₂O₃ catalyst the temperature had to be raised to 184° C. to get higher conversions (93%). Under these conditions the selectivity to dibutylamine was low at 72%.

Table 8 also gives the conversion as a function of temperature for cobalt based catalysts. At 165° C. both 20%Co/ tiary amines at higher conversions. The Ni-Ru bimetallic catalyst also gives higher secondary amines at higher conversions. Based on these results the 20%Ni/1%Ru/Al₂O₃ catalyst is the most preferred catalyst to convert primary amines into secondary amines in high selectivity in fixed bed.

What is claimed is:

1. In a process for the production of amines by the catalytic disproportionation of a feedstock containing a primary amine to produce a reaction product containing a secondary amine wherein a feed stock containing an aliphatic primary amine is contacted with hydrogen in the presence of a hydrogenation catalyst under conditions for effecting disproportionation of said primary amine to produce said secondary amine, the improvement which comprises:

disproportionating a feedstock consisting essentially of an aliphatic primary monoamine having from 2 to 10 carbon atoms; and, utilizing a catalyst comprising cobalt or nickel in combination with at least one other metal selected from the group consisting of rhodium, palladium, ruthenium or platinum.

2. The process of claim 1 wherein said catalyst is a bimetallic catalyst comprising nickel or cobalt in combination with rhodium, ruthenium or palladium carried on a support.

3. The process of claim 2 wherein the bimetallic catalyst comprises 1–60% by weight nickel or cobalt and from 0.01 to 10% by weight of rhodium, ruthenium or palladium.

4. The process of claim 3 wherein the bimetallic catalyst consists essentially of nickel in combination with rhodium, ruthenium or palladium.

5. The process of claim 4 wherein said nickel is present in an amount from about 5 to 25% by weight and the rhodium, ruthenium or palladium is present in an amount from about 0.5 to 2,5% and the temperature for disproportionation is from 140° to 220° C. and the pressure is from about 50 to 500 psig.

6. The process of claim 5 wherein said support is alumina.

7. The process of claim 6 wherein the feedstock containing said aliphatic primary monoamine is obtained by the hydrogenation of a nitrile selected from the group consisting of acetonitrile, propionitrile, and butyronitrile.

8. The process of claim 7 wherein the nickel component of the catalyst is present in an amount from about 5 to 25% by weight and the rhodium or palladium is present in an amount from about 0.5 to 2.5 % by weight.

9. The process of claim 6 wherein the catalyst consists essentially of nickel and palladium.

10. The process of claim 3 wherein the catalyst consists essentially of cobalt in combination with rhodium or palladium.

11. The process of claim 10 wherein said cobalt is present in an amount from about 5 to 25% and the rhodium or palladium is present in an amount from about 0.5 to 2.5%.

* * * * *